United States Patent [19]

Thorwart et al.

[11] Patent Number: 4,891,374
[45] Date of Patent: Jan. 2, 1990

[54] IMIDAZO- AND TRIAZOLOTHIADIAZINES

[75] Inventors: Werner Thorwart, Hochheim am Taunus; Ulrich Gebert, Kelkheim; Rudolf Schleyerbach, Hofheim am Taunus; Robert R. Bartlett, Darmstadt, all of Fed. Rep. of Germany

[73] Assignee: Hoechst Aktiengesellschaft, Frankfurt am Main, Fed. Rep. of Germany

[21] Appl. No.: 149,546

[22] Filed: Jan. 28, 1988

[30] Foreign Application Priority Data

Jan. 30, 1987 [DE] Fed. Rep. of Germany ....... 3702757

[51] Int. Cl.$^4$ ..................... C07D 513/04; A61K 31/54
[52] U.S. Cl. ..................................... 514/222.8; 544/10
[58] Field of Search ........................ 514/222.8; 544/10

[56] References Cited

FOREIGN PATENT DOCUMENTS 1620071 12/1969 Fed. Rep. of Germany .

OTHER PUBLICATIONS

Pyl, et al., Liebigs Ann. Chem., vol. 663, 1963, pp. 113–119.
Bulka et al., Z. Chem., vol. 15, No. 12, 1975, p. 482.
El-Dawy et al., Journal of Pharmaceutical Sciences, vol. 72, No. 1, 193, pp. 45–50 (1983).
Brune, Eur. J., Rheumatol. Inflamm., vol. 5, 1982, pp. 335–349.
Chemical Abstract, vol. 59, No. 5160 (1963), Pyl et al.
Chemical Abstract, vol. 70, No. 96771w (1969), Westphal et al.
Chemical Abstract, vol. 104, No. 50789a (1986).
Chemical Abstract, vol. 90, No. 114920p (1979), Van der Goot et al.

Primary Examiner—John M. Ford
Attorney, Agent, or Firm—Finnegan, Henderson, Farabow, Garrett and Dunner

[57] ABSTRACT

Novel imidazo- and triazolothiadiazines of the general formula I

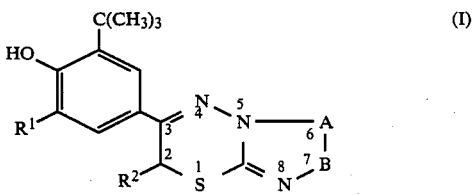

in which
$R^1 = C_1$–$C_4$-alkyl,
$R^2 = H$ or $C_1$–$C_3$-alkyl
and the structural element —A—B—=—CH$_2$—CH$_2$—, —CH=CH—, —CH=N—, —CH$_2$—CO— or —CO—CH$_2$—,
and the physiologically aceptable acid-addition salts thereof, are prepared by reacting 2-halo-1-phenylalkanones of the formula II

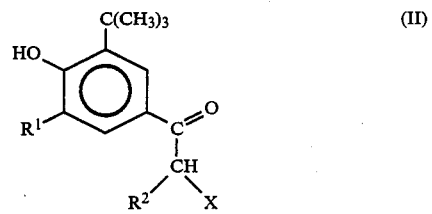

(meaning of $R^1$ and $R^2$ as in formula I, X=halogen) with compounds of the formula III

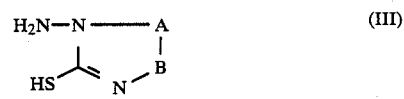

(meaning of —A—B— as in formula I) and, if appropriate, converting the compounds of the formula I formed into the physiologically acceptable acid-addition salts thereof by means of suitable acids.

The compounds of the formula I and the physiologically acceptable acid-addition salts thereof are principally suitable for the prevention and treatment of inflammatory—in particular inflammatory rheumatic—disorders.

Some of the intermediates formed during the preparation of the compounds of the formula I are also novel, namely 1-amino-2-mercaptoimidazole

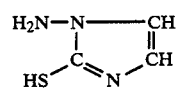

and 1-amino-2-thioxo-5-imidazolidinone

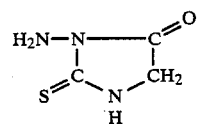

10 Claims, No Drawings

IMIDAZO- AND TRIAZOLOTHIADIAZINES

The present invention relates to novel imidazo- and triazolothiadiazines, a process for the preparation thereof, and the use thereof as active compounds in medicaments for the treatment of inflammatory disorders, in particular inflammatory rheumatic disorders; in addition, the invention also relates to some intermediates formed in the preparation of the abovementioned imidazo- and thiazolothiadiazines.

The non-steroidal antiphlogistics preferably employed hitherto in rheumatherapy are almost exclusively relatively strong cyclooxygenase inhibitors, which inhibit endogenic degradation of arachidonic acid to give inflammation- and pain-promoting prostaglandins However, a number of serious side effects, such as gastrointestinal complaints, renal disfunctions and allergic reactions (for example skin allergies and asthmatic attacks), which frequently cause termination of the therapy, in particular during the long-term treatment which is usually necessary, are causally associated with excessive inhibition of the cyclooxygenase activity (cf. K. Brune, Eur. J. Rheumatol. Inflam. 5 (1982), pp. 335–349).

A further disadvantage of these classical non-steroidal antiphlogistics which is causally associated with the described mechanism of action is that, although they permit elimination or alleviation of the pain, inflammation and swelling symptoms, they do not affect the immunopathological processes underlying the inflammatory rheumatic disorders and therefore are not capable of halting the course of the advanced disease.

There is thus an urgent demand for therapeutically useful antirheumatics which, on the basis of a more favorable profile of action, differ advantageously from the known nonsteroidal antiphlogistics through better compatibility on the one hand and a more causal engagement in the rheumatic pathological process on the other. Promising starting points for these medicaments are pharmaceuticals which engage to an increased extent in the alternative route of arachidonic acid degradation, for example by inhibiting 5-lipoxygenase and thus suppressing excessive formation of the pro-inflammatory leucotrienes, deactivating highly reactive oxygen radicals, which, as inflammation mediators, perpetually sustain cell and tissue destruction in the inflammatory rheumatic joints, and/or restoring the impaired immune system and thus opening up the possibility of using medicaments to treat the rheumatic disorders more causally.

Surprisingly, it has now been found that, by introducing certain 3-alkyl-5-tert.butyl-4-hydroxyphenyl radicals into the 3-position of optionally 2-substituted 2H-imidazo[2,1-b]-[1,3,4]thiadiazines and 2H-s-triazolo[3,4-b][1,3,4]thiadiazines, novel compounds are obtained which, due to their pharmacological properties, meet the demands set above and accordingly are highly suitable for treatment of rheumatic disorders.

In contrast to the known non-steroidal antiphlogistics, the compounds, which are also extremely well tolerated gastrically, inhibit the arachidonic acid-degrading enzyme 5-lipoxygenase, while an effect on cyclooxygenase cannot be detected. The ability of the compound to deactivate oxygen radicals is apparent, for example, in the model of inflammation induced by (R)Adriamycin (Messrs. Farmitalia) and through the inhibition of lipid peroxidation.

In addition, they engage advantageously in the impaired immune system, as can be demonstrated by the normalization of suppressed immune activity in pathological models of arthritis induced using Freund's adjuvant or type II collagen.

The 2H-imidazo[2,1-b][1,3,4]thiadiazines already described in the literature are all 3,7-diphenylated derivatives of which no pharmacological properties are known (Th. Pyl, Fr. Waschk and H. Beyer, Liebigs Ann. Chem. 663 (1963), pp. 113–119, and E. Bulka and W. D. Pfeiffer, Z. Chem. 15 (1975), p. 482). From the same ring system are derived the partially hydrogenated 6,7-dihydro-2H-imidazo[2,1-b][1,3,4]-thiadiazines and their 6- and 7-oxo derivatives, which have hitherto not been described in the literature and whose derivatives with the 3-alkyl-5-tert.butyl-4-hydroxyphenyl radical in the 3-position are covered by the present invention. Of the structurally closely related 2H-s-triazolo-[3,4-b][1,3,4]thiadiazines, diphenyl derivatives are likewise known (M. A. El-Dawy et al., J. Pharm. Sci. 72 (1983), pp 45–50), which are said to have an anthelmintic activity.

In contrast, the present invention relates to novel 2H-imidazo[2,1-b][1,3,4]thiadiazines and 2H-s-triazolo[3,4-b]-[1,3,4]thiadiazines which carry a 3-alkyl-5-tert.butyl-4-hydroxyphenyl radical as the essential pharmacophoric group in the 3-position and optionally carry a further substituent in the 2-position. Due to their abovementioned pharmacological properties, the compounds according to the invention are suitable for use in medicaments, in particular in those which are indicated in inflammatory rheumatic disorders.

The invention thus relates to novel imidazo- and triazolothiadiazines of the general formula I

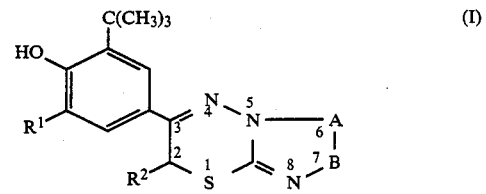

in which
$R^1$ denotes a straight-chain or branched alkyl group having 1 to 4 carbon atoms and
$R^2$ denotes a hydrogen atom or an alkyl radical having 1 to 3 carbon atoms, and the two-membered structural element
—A—B— in the five-membered ring represents —CH$_2$—CH$_2$—, —CH=CH—, —CH=N—, —CH$_2$—CO— or —CO—CH$_2$—, and the physiologically acceptable acid-addition salts thereof.

Preferred compounds of the formula I here are those in which the structural element —A—B— denotes an ethylene or vinylene group or either A or B represents a carbonyl group and the other bridging member represents a methylene group. Of these compounds, those in which $R^1$ denotes a tert.butyl radical and $R^2$ represents hydrogen or methyl, such as, for example, 3-(3,5-di-tert.butyl-4-hydroxyphenyl)-6,7-dihydro-2H-imidazo[2,1-b][1,3,4]thiadiazine, should in turn be emphasized.

Methyl, ethyl, n-propyl, isopropyl, n-butyl, isobutyl, sec.butyl and tert.butyl are suitable alkyl radicals for the group $R^1$, and methyl, ethyl, n-propyl and isopropyl are suitable alkyl radicals for the group $R^2$.

The invention furthermore relates to a process for the preparation of the novel imidazo- and triazolothiadiazines and their physiologically acceptable acid-addition salts, which comprises reacting a 2-halo-1-phenylalkanone of the formula II

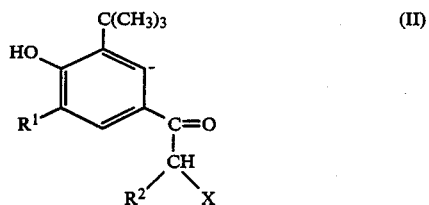

in which $R^1$ and $R^2$ have the abovementioned meaning and X represents a halogen atom, preferably chlorine or bromine, with a compound of the formula III

in which the two-membered structural element —A—B— has the abovementioned meanings, to give compounds of the formula I according to the invention, and either isolating the latter in free form or converting them into physiologically acceptable addition salts using suitable acids.

Mineral acids, such as hydrobromic acid, hydrochloric acid, sulfuric acid or phosphoric acid; organic acids, such as acetic acid, lactic acid, maleic acid, fumaric acid, oxalic acid, tartaric acid, citric acid or gluconic acid; or other physiologically acceptable acids, such as sulfonic acids, for example benzenesulfonic acid, p-toluenesulfonic acid, methanesulfonic acid, trifluoromethylsulfonic acid and cyclohexylamidosulfonic acid, for example, are suitable for the preparation of acid-addition salts.

The 2-halo-1-phenylalkanones of the formula II used as starting materials for the process according to the invention are known from the literature or can easily be prepared from 1-(3-alkyl-5-tert.butyl-4-hydroxyphenyl)-alkanones through reaction with a suitable halogenating agent by methods described in Houben-Weyl, Vol. V/4 (1960), pp. 171-189. Suitable compounds II which may be mentioned as examples are 2-bromo-1-(3,5-di-tert.butyl-4-hydroxyphenyl)ethanone and 2-bromo-1-(5-tert.butyl-3-methyl-4-hydroxyphenyl)-ethanone, which can be prepared by halogenation of the correspondingly substituted 1-phenylalkanones using elemental bromine or using copper(II) bromide by a process of L. C. King and G. K. Ostrum, J. Org. Chem. 29 (1964), pp. 3459-3461.

Especially suitable for obtaining those compounds of the formula II in which X represents a chlorine atom is sulfuryl chloride, which is preferably brought to reaction with the appropriate 1-phenylalkanones at temperatures between about 10° to 30° C. in the presence of inert solvents, such as, for example, methylene chloride or chloroform. A further preparation process comprises Friedel-Crafts acylation of 2-alkyl-6-tert.butylphenols by means of, preferably, chloroacetyl chloride in the presence of Lewis acids, such as, for example, aluminum chloride or boron trifluoride.

Of the compounds of the formula III which are likewise employed as starting materials, the following heterocyclic compounds are known from the Literature: 1-amino-2-thioxoimidazolidine (K. H. Mayer and S. Petersen, Synthesis 1971, pp. 370-373, 4-amino-3-mercapto-1,2,4-triazole (H. Beyer and C.F. Kröger, Liebigs Ann. Chem. 637 (1960), pp. 135-145) and 1-amino-2-thioxo-4-imidazolidinone (H. Shirai and T. Yashiro, Yakugaku Zasshi 87 (1967), pp. 137-142).

By contrast, 1-amino-2-mercaptoimidazole, which can easily be prepared from thioisocyanatoacetaldehyde dialkyl acetals and hydrazine, preferably in solvents, such as methanol or ethanol, containing hydrochloric acid, at reaction temperatures above about 30° C., is novel.

Alkaline cyclization of alkyl, preferably ethyl, thiosemicarbazido-(4)-acetate by means of sodium alcoholate gives 1-amino-2-thioxo-5-imidazolidinone, which is likewise novel.

The reaction of 2-halo-1-phenylalkanones II with compounds of the formula III is expediently carried out using equimolar amounts of the two reactants in a solvent or diluent which is inert towards the reactants. Suitable for this purpose are, in particular, polar solvents, for example lower aliphatic alcohols, such as methanol, ethanol, the various propanols or butanols, or lower aliphatic carboxylic acids, such as acetic acid, and mixtures of the solvents mentioned or mixtures thereof with water. However, ethylene glycol and its ethers, ethyl acetate, acetone, butan-2-one, dimethylformamide or acetonitrile can also be used. The reaction temperatures are generally between about 20° C. and the boiling point of the particular reaction medium used. The reaction mixture is preferably heated to the boiling point when working in ethanol and to temperatures between about 70° and 100° C. when working in acetic acid, the reaction times being between less than one hour and about 12 hours.

Due to their valuable pharmacological properties and, at the same time, excellent tolerability, the imidazo- and triazolothiadiazines of the formula I according to the invention and their physiologically acceptable acid-addition salts are particularly suitable for use as active compounds in medicaments, in particular in those for treatment of inflammatory rheumatic disorders. They can either be administered alone, for example in the form of microcapsules, in mixtures with one another or in combination with suitable adjuvants and/or excipients.

The invention thus also relates to medicaments which comprise at least one compound of the formula I, if appropriate in the form of one of its acid-addition salts, or contain at least one of these active compounds in addition to pharmaceutically suitable and physiologically acceptable excipients, diluents and/or other adjuvants.

The medicaments according to the invention can be administered orally, topically, rectally or, if desired, parenterally, oral administration being preferred.

Suitable solid or liquid galenic formulations are, for example, granules, powders, coated tablets, tablets, (micro)capsules, suppositories, syrups, elixirs, suspensions, emulsions, drops or injectable solutions, and also preparations having a protracted release of the active compound, in the production of which adjuvants, such as excipients, disintegrants, binders, coating agents, swelling agents, glidants or lubricants, flavors, sweeteners or solubilizers are usually used. Frequently used adjuvants which may be mentioned are, for example, magnesium carbonate, titanium dioxide, lactose, mannitol and other sugars, talc, lactalbumin, gelatin, starch, cellulose and its derivatives, animal and vegetable oils, polyethylene glycols and solvents, such as, for example, sterile water and monohydric or polyhydric alcohols, for example glycerol.

The pharmaceutical preparations are preferably produced and administered in dosage units, each unit containing as active component a certain dose of at least one compound of the formula I and/or at least one of its physiologically acceptable acid-addition salts. In the case of solid dosage units, such as tablets, capsules, coated tablets or suppositories, this dose may be up to 800 mg, but preferably about 100 to 500 mg.

For treatment of an adult patient suffering from inflammatory rheumatic disorders, daily doses from about 100 to 2000 mg of active compound, preferably about 300 to 1000 mg, are indicated in the case of oral administration - depending on the activity on humans of the compounds of the formula I and/or of the corresponding acid-addition salts. However, higher or lower daily doses may be appropriate under certain circumstances. Administration of the daily dose can take place either by single administration in the form of a single dosage unit or several smaller dosage units or by multiple administration of divided doses at certain intervals.

Finally, in the production of the abovementioned galenic preparation forms, the compounds of the formula I and the corresponding acid-addition salts thereof can also be formulated together with other suitable active compounds, for example antiuricopathics, thrombocyte-aggregation inhibitors, analgesics and other steroidal or non-steroidal antiphlogistics.

The structure of all the compounds described below has been confirmed by elemental analysis and IR and $^1$H NMR spectra.

EXAMPLE 1

3-(3,5-Di-tert.butyl-4-hydroxyphenyl)-6,7-dihydro-2H-imidazo[2,1-b][1,3,4]thiadiazine hydrochloride (a)
2-Bromo-1-(3,5-di-tert.butyl-4-hydroxyphenyl)-ethanone

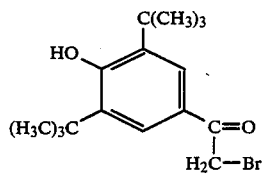

206 g (0.83 mol) of 1-(3,5-di-tert.butyl-4-hydroxyphenyl)ethanone are dissolved in 415 ml of methylene chloride while stirring, the mixture is heated to boiling, and 144 g (0.9 mol) of bromine are added dropwise over the course of 30 minutes. The mixture is then refluxed for a further 2 hours and cooled, 400 ml of water are added, and the organic phase is separated off and dried over sodium sulfate. After the solvent had been removed under reduced pressure, the solid crude product obtained was recrystallized from 540 ml of methylcyclohexane.

Yield: 191 g (67% of theory). Melting point: 105°-108° C. $C_{16}H_{23}BrO_2$ (MW=327.3).

(b)
3-(3,5-di-tert.butyl-4-hydroxyphenyl)-6,7-dihydro-2Himidazo[2,1-b][1,3,4]thiadiazine hydrochloride

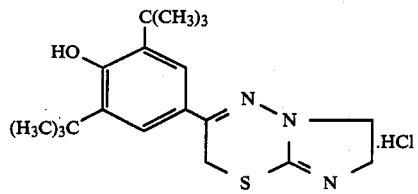

65.5 g (0.2 mol) of 2-bromo-1-(3,5-di-tert.butyl-4-hydroxyphenyl)-ethanone from step (a) and 23.4 g (0.2 mol) of 1-amino-2-thioxoimidazolidine were dissolved in 600 ml of ethanol and heated to boiling for 2 hours. The precipitate produced during this procedure was filtered off under suction, taken up in 500 ml of water and rendered alkaline using 2N sodium hydroxide solution. Extraction with dichloromethane, drying the organic phase over sodium sulfate and concentration under reduced pressure gave 57.1 g of the free base. The product was dissolved in 250 ml of chloroform and converted into the hydrochloride by means of ethereal hydrochloric acid, and the crystalline precipitate was filtered off under suction and dried in vacuo.

Yield: 73.6 g (95.5 % of theory). Melting point: 262°-264° C. (decomp). $C_{19}H_{28}ClN_3OS$ (MW=382.0).

Analysis: Calculated: C 59.75%; H 7.39%; Cl 9.28%; N 11.00%; S 8.39%. Found: C 59.77%; H 7.62%; Cl 9.55%; N 11.03%; S 8.43%.

EXAMPLE 2

3-(3,5-Di-tert.butyl-4-hydroxyphenyl)-2-methyl-6,7-dihydro-2H-imidazo[2,1-b][1,3,4]thiadiazine hydrochloride (a)
2-Bromo-1-(3,5-di-tert.butyl-4-hydroxyphenyl)-propanone

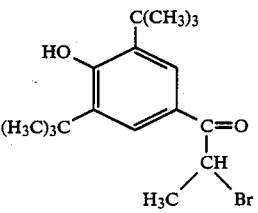

A solution of 82.0 g (0.31 mol) of 1-(3,5-di-tert.butyl-4-hydroxyphenyl)-propanone in 300 ml of chloroform was added dropwise while stirring to a boiling suspension of 139.0 g (0.62 mol) of copper(II) bromide in 300 ml of ethyl acetate. The mixture was subsequently refluxed for 3 hours until the evolution of hydrogen bromide was complete. After the mixture had been cooled to room temperature, the copper salts were filtered off under suction, the filter residue, was washed twice with ethyl acetate, and the filtrate was evaporated under reduced pressure. The solid residue was recrystallized from petroleum ether (40°-60° C.).

Yield: 87.5 g (82% of theory). Melting point: 130°-132° C. $C_{17}H_{25}BrO_2$ (MW=341.3).

(b) 3-(3,5-Di-tert.butyl-4-hydroxyphenyl)-2-methyl-6,7-dihydro-2H-imidazo[2,1-b][1,3,4]thiadiazine hydrochloride

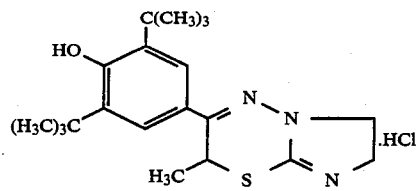

17.1 g (0.05 mol) of 2-bromo-1-(3,5-di-tert.butyl-4-hydroxyphenyl)-propanone from step (a) and 5.5 g (0.047 mol) of 1-amino-2-thioxoimidazolidine were refluxed for 5 hours in 50 ml of ethanol. After cooling, the solution was evaporated, 200 ml of water were added to the residue, and the mixture was rendered alkaline using 2N sodium hydroxide solution. Extraction with dichloromethane, drying and evaporation gave an oily crude base, which was dissolved in 100 ml of ethyl acetate, and isolated as the hydrochloride after addition of an equimolar amount of ethereal hydrochloric acid.

Yield: 14.4 g (77.4% of theory). Melting point: 247°–249° C. $C_{20}H_{30}ClN_3OS$ (MW=396.0).

Analysis: Calculated: C 60.66%; H 7.64%; Cl 8.95%; N 10.61%; S 8.10%. Found: C 60.44%; H 7.66%; Cl 9.28%; N 10.56%; S 7.98%.

EXAMPLE 3

3-(5-tert Butyl-3-methyl-4-hydroxyphenyl)-6,7-dihydro-2H-imidazo[2,1-b][1,3,4]thiadiazine hydrochloride (a) 2-Bromo-1-(5-tert.butyl-3-methyl-4-hydroxyphenyl)ethanone

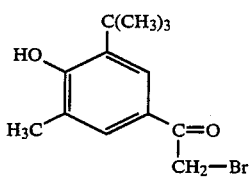

A solution of 82.5 g (0.4 mol) of 1-(5-tert.butyl-3-methyl-hydroxyphenyl)-ethanone in 360 ml of chloroform was added dropwise while stirring to a suspension, heated to boiling, of 179 g (0.8 mol) of copper(II) bromide in 360 ml f ethyl acetate. The mixture was subsequently refluxed for 4 hours until the evolution of hydrogen bromide was complete. After the mixture had been cooled to room temperature, the copper salts were filtered off under suction, the filter residue was washed repeatedly with ethyl acetate, the filtrate was evaporated under reduced pressure, the solid residue was recrystallized from cyclohexane.

Yield: 81.9 g (72% of theory). Melting point: 90°–92° C. $C_{13}H_{17}BrO_2$(MW=285.2)

(b) 3-(5-tert.Butyl-3-methyl-4-hydroxyphenyl)-6,7-dihydro2H-imidazo[2,1-b][1,3,4]thiadiazine hydrochloride

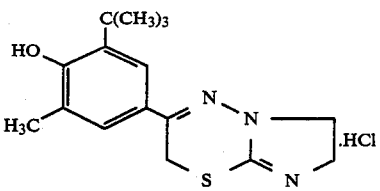

18.3 g (0.064 mol) of 2-bromo-1-(5-tert.butyl-3-methyl-4-hydroxyphenyl)-ethanone from step (a) and 7.0 g (0.06 mol) of 1-amino-2-thioxoimidazolidine were dissolved in 180 ml of ethanol, and the mixture was refluxed for 2 hours. After the reaction mixture had been evaporated to dryness, the residue was taken up in 200 ml of water, neutralized by means of 2N sodium hydroxide solution and extracted three times by shaking with chloroform. The combined organic extracts were evaporated, the residue was dissolved in 200 ml of boiling ethanol, and ethanolic hydrochloric acid was added. The hydrochloride produced in crystalline form by this operation was filtered off and recrystallized from isopropanol.

Yield: 15.7 g (77% of theory). Melting point: 234° C. (decomp.). $C_{16}H_{22}ClN_3OS$ (MW=339.9).

Analysis: Calculated: C 56.55%; H 6.53%; Cl 10.43%; N 12.36%; S 9.43%. Found: C 56.23%; H 6.46%; Cl 10.16%; N 12.62%; S 9.39%.

EXAMPLE 4

3-(3,5-Di-tert.butyl-4-hydroxyphenyl)-2H-imidazo[2,1-b][1,3,4]thiadiazine hydrochloride (a) 1-Amino-2-mercaptoimidazole hydrochloride.

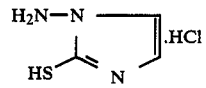

A solution of 134 g (0.9 mol) of thioisocyanatoacetaldehyde dimethyl acetal was added dropwise to a solution of 29 ml (0.9 mol) of anhydrous hydrazine in 180 ml of ethanol while cooling in an ice bath at a rate such that the reaction temperature did not exceed 30° C. After the mixture had been refluxed for 2 hours and subsequently cooled to room temperature, 113 ml of concentrated hydrochloric acid were added dropwise, and the mixture was heated to boiling for a further 2 hours. The precipitate formed during this operation was filtered off under suction and recrystallized from isopropanol.

Yield: 123.7 g (91 % of theory). Melting point: 167°–168° C. $C_3H_6ClN_3S$ (MW =151.6).

(b) 3-(3,5-Di-tert.butyl-4-hydroxyphenyl)-2H-imidazo[2,1-b][1,3,4]thiadiazine hydrochloride

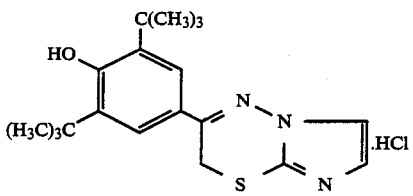

A solution of 18.0 g (0.055 mol) of 2-bromo-1-(3,5-ditert.butyl-4-hydroxyphenyl)-ethanone and 7.6 g (0.05 mol) of 1-amino-2-mercaptoimidazole hydrochloride from step (a) in 150 ml of ethanol was refluxed for 9 hours. The residue remaining after evaporation of the solution was rendered alkaline by means of 50 ml of 2N sodium hydroxide solution and extracted with chloroform. In order to convert the product into the hydrochloride, an equimolar amount of ethereal hydrochloric acid was added to the dried chloroform phase, and the batch of crystals produced was filtered off under suction and crystallized from ethanol.

Yield: 12.0 g (63% of theory). Melting point: 219°–220° C. $C_{19}H_{26}ClN_3OS$ (MW =380.0).

Analysis: Calculated: C 60.06%; H 6.90%; Cl 9.33%; N 11.06%; S 8.44%. Found: C 60.09%; H 6.98%; Cl 9.47%; N 11.01%; S 8.51%.

3-(3,5-Di-tert.butyl-4-hydroxyphenyl)-2-methyl-2H-imidazo[2,1-b][1,3,4]thiadiazine hydrochloride of melting point 202°–205° C. was formed analogously to Example 4 from 2-bromo-1-(3,5-di-tert.butyl-4-hydroxyphenyl)-propanone of Example 2(a) and 1-amino-2-mercaptoimidazole.

EXAMPLE 5

3-(3,5-Di-tert.butyl-4-hydroxyphenyl)-2-methyl-2H-s-triazolo[3,4-b][1,3,4]thiadiazine

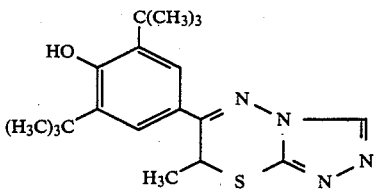

19.0 g (0.056 mol) of 2-bromo-1-(3,5-di-tert.butyl-4-hydroxyphenyl)-propanone from Example 2(a) and 5.8 g (0.05 mol) of 4-amino-3-mercapto-1,2,4-triazole were refluxed for 5 hours in 120 ml of ethanol, and, after cooling, the reaction mixture was evaporated to dryness. After 100 ml of ethyl acetate were added and on vigorous stirring, the oily residue solidified to form a batch of crystals, which was then recrystallized from isopropanol.

Yield: 12.9 g (72% of theory). Melting point: 195° C. $C_{19}H_{26}N_4OS$ (MW=358.5)

Analysis: Calculated: C 63.66%; H 7.31%; N 15.63%; S 8.94%. Found: C 63.90%; H 7.48%; N 15.61%; S 9.02%.

The preparation of 3-(3,5-di-tert.butyl-4-hydroxyphenyl)-H-s-triazolo[-3,4-b][1,3,4]thiadiazine of melting point 263° C. from 2-bromo-1-(3,5-di-tert.butyl-4-hydroxyphenyl)ethanone of Example 1(a) and 4-amino-3-mercapto-1,2,4-triazole took place in accordance with Example 5.

EXAMPLE 6

3-(3,5-Di-tert.butyl-4-hydroxyphenyl)-7-oxo-6,7-dihydro-2H-imidazo[2,1-b][1,3,4]-thiadiazine hydrobromide

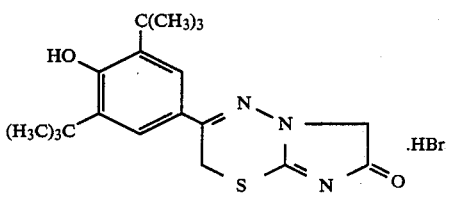

36.0 g (0.11 mol) of 2-bromo-1-(3,5-di-tert.butyl-4-hydroxyphenyl)-ethanone from Example 1(a) and 16.7 g (0.1 mol) of 1-amino-2-thioxo-4-imidazolidinone were warmed to 90° C. while stirring in 300 ml of glacial acetic acid. After a clear solution had been produced in the course of about 20 minutes, the mixture was allowed to cool to room temperature. The crystals produced during this cooling were filtered off under suction and recrystallized from glacial acetic acid.

Yield: 29.5 g (67% of theory). Melting point: 208°–209° C. (decomp.). $C_{19}H_{26}BrN_3O_2S$ (MW=440.4).

Analysis: Calculated: C 51.82%; H 5.95%; Br 18.14%; N 9.54%; S 7.28%. Found: C 51.89%; H 5.88%; Br 17.85%; N 9.46%; S 7.43%.

EXAMPLE 7

3-(3,5-Di-tert.butyl-4-hydroxyphenyl)-6-oxo-6,7-dihydro-2H-imidazo[2,1-b][1,3,4]thiadiazine hydrobromide (a) 1-Amino-2-thioxo-5-imidazolidinone

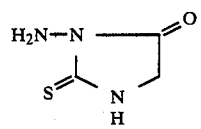

21.6 g (0.12 mol) of ethyl thiosemicarbazido-(4)-acetate in 285 ml of ethanol were refluxed for 15 minutes after 7.1 ml of 1N sodium ethanolate solution had been added. After 7 ml of 1N hydrochloric acid and a further 660 ml of ethanol were added to the still-hot solution, the mixture was heated briefly until the precipitate produced had dissolved completely. After the mixture had been stirred for 6 hours at room temperature, the yellowish crystals which had precipitated were filtered off, washed with ethanol and diethyl ether, and dried in vacuo.

Yield: 13.8 g (88% of theory). Melting point: 168°–169° C. $C_3H_5N_3OS$ (MW=131.2).

(b)
3-(3,5-Di-tert.butyl-4-hydroxyphenyl)-6-oxo-6,7-dihydro-2H-imidazo[2,1-b][1,3,4]thiadiazine hydrobromide

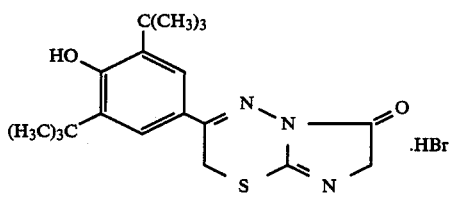

34.4 g (0.11 mol) of 2-bromo-1-(3,5-di-tert.butyl-4-hydroxyphenyl)-ethanone from Example 1(a) and 13.8 g (0.11 mol) of 1-amino-2-thioxo-5-imidazolidinone from step (a) were heated at 90° C. for 30 minutes in 300 ml of glacial acetic acid. After cooling, the precipitate was filtered off and washed with 250 ml of ethyl acetate, and the crystals were dried in vacuo over phosphorus pentoxide.

Yield: 30.4 g (63% of theory). Melting point: 235°–236° C. (decomp.). $C_{19}H_{26}BrN_3O_2S$ (MW=440.4).

Analysis: Calculated: C 51.82%; H 5.95%; Br 18.14%; N 9.54%; S 7.28%. Found: C 51.51%; H 5.74%; Br 17.74%; N 9.28%; S 7.24%.

Pharmacological testing and results

The compounds of the formula I according to the invention were tested for antiphlogistic action, influence on immunopathological processes, oxygen radical-deactivating potency, ulcerogenic activity and acute toxicity in the animal models described below, the antiphlogistic naproxen (2-(6-methoxy2-naphthyl)-propionic acid), which is amongst the first choice standard preparations in rheumatherapy, being included in the investigations as the comparison substance.

1. Adjuvant arthritis

The investigations were carried out using the method of Pearson (Arthrit. Rheum. 2 (1959), p. 44). The experimental animals used were male rats of the Wistar-Lewis strain having a body weight between 130 and 200 g. Compounds to be tested were administered orally (p.o.) once daily from day 1 to day 5 of the experiment in doses of 50 mg per kg of body weight. The animals in a control group were given only the vehicle. Each preparation group and the control group contained 8 animals. The criterion used to determine the action was the percentage reduction in the increase in paw volume compared to that of the untreated control group.

2. Acute gastral ulcerogenity

The investigation was in each case carried out on 10 male Sprague-Dawley rats whose gastric mucous membrane had been sensitized by hunger stress. The body weight of the animals was between 200 and 300 g. While allowing free access to the drinking water, the feed was withdrawn 48 hours before administration of the test preparations until sacrifice of the animals. The rats were sacrificed 24 hours after oral administration of the substance, and the stomachs were removed, cleaned under running water and inspected for mucous membrane lesions. All macroscopically visible lesions were regarded as ulcers. The number of animals having ulcers was determined per dose, and this figure was used to calculate, by the method of Litchfield and Wilcoxon (J. Pharmacol. Exp. Ther. 96 (1949), p. 99), the $UD_{50}$ values, ie. the doses at which lesions were caused in 50% of the animals.

3. Acute toxicity

The $LD_{50}$ values were determined by standard methods from the mortality occurring within 7 days in NMRI (Naval Medical Research Institute) mice (6 animals per dose) after a single intraperitoneal (i.p.) administration. The results of these investigations, which clearly support the superiority of the compounds of the formula I according to the invention over the standard preparation naproxen, are collated in Table 1 below.

TABLE 1

Antiphlogistic action, ulcerogenity and acute toxicity

| Compound from Example | Adjuvant Arthritis (% inhibition at 50 mg/kg p.o.) | Acute ulcerogenity $UD_{50}$ (mg/kg) | Acute toxicity $LD_{50}$ (mg/kg) |
|---|---|---|---|
| 1 | 62 | 400 | >1200 |
| 2 | 63 | 200 | >1200 |
| 4 | 69 | >200* | 300–600 |
| 5 | 56 | >200* | >1200 |
| 6 | 73 | >200* | 300–600 |
| 7 | 59 | >200* | 300–600 |
| naproxen | 55 | 23 | 500 |

*in each case the maximum dose administered

The superiority of the compounds according to the invention is particularly striking in the comparison of the gastral tolerance, which has a decisive clinical importance in the treatment of inflammatory rheumatic disorders using nonsteroidal antiphlogistics.

The compounds according to the invention also proved to be clearly superior to the standard preparation naproxen in further specific experiments.

4. Inhibition of immunopathological processes

It is generally accepted today that the advanced course of inflammatory rheumatic disorders is caused mainly by disfunctions in the immune system and that causal therapy can only succeed using medicaments which are capable of interrupting these immunopathological processes.

(a) Adjuvant arthritis

In the rat model described under point 1 of arthritis induced using Freund's adjuvant, the immune activity of lymphocytes towards certain mitogens, such as concavalin A, phytohemagglutinin A and dextran sulfate, is generally drastically reduced. The stimulating action on this greatly suppressed immunological response was therefore investigated. In this investigation, the compound from Example 1, for example, caused substantial normalization of the immunoreactivity after oral administration of 20 mg/kg, whereas naproxen, which was tested in doses up to 25 mg/kg, was ineffective.

(b) Type II collagen-induced arthritis

In this experiment, arthritis was induced in male Wistar rats by means of type II collagen, which could be obtained by standard methods of Miller and Rhodes (Meth. Enzymol. 82 (1982), p. 33) from the nasal septum of the calf and, mixed with Freund's incomplete adjuvant, was injected intradermally into the animals. This immunization procedure was repeated 7 days later. 20 days after the initial immunization, the sick rats were divided into groups each containing 7 animals, which, in the subsequent 20-day treatment phase, received the respective test substance or the pure vehicle (control group) once daily orally.

On day 41 of the experiment, ie. one day after the final administration of substance, lymphocytes were obtained from the spleen of the experimental animals and their immune activity towards mitogens was investigated, since the immune status of lymphocytes is also sensitively impaired in this model.

It was again possible to detect dose-dependent curative effects for the compounds according to the invention on the greatly weakened immune system, whereas naproxen exhibited no action. Thus, for example, using a dose of 25 mg/kg p.o. of the compound from Example 1, the immune function of both T and B lymphocytes was completely normalized.

5 Antioxidative action

According to current opinion, aggressive oxygen radicals, which are formed to excess during the chronic inflammation process and, as highly toxic inflammation mediators themselves, perpetually maintain the destruction of connective tissue which proceeds via irreversible lipid peroxidation of the cell membranes, participate prominently in the progressive course, caused by a number of factors, of rheumatoid arthritis and other inflammatory disorders. As a consequence, pharmaceuticals having an antioxidative action and having the capability to deactivate these extremely cytotoxic oxygen radicals should allow specific intervention in the chronic course of the inflammation. A suitable animal model for this type of tissue destruction caused by oxygen radicals is Adriamycin (doxorubicin) induced inflammation in the rat.

(a) Adriamycin-induced inflammation

The investigations were carried out using the method of D. M. Siegel et al. (Inflammation 4 (1980), p. 233) on male Sprague-Dawley rats having a body weight between 200 and 230 g in groups each containing 7 animals, which received 0.1 mg of Adriamycin, dissolved in 0.1 ml of 0.9% strength sodium chloride solution, by means of subcutaneous injection into the left rear paw. The increase in paw volume was determined 72 hours later by plethysmographic measurement as a measure of the degree of inflammation.

The test preparations were administered orally in 1% strength aqueous carboxymethylcellulose suspension once daily on 4 successive days, starting with the day of Adriamycin injection.

In this test too, the compound from Example 1, for example, exhibited a dose-dependent protective effect against Adriamycin-induced tissue destruction, which reached an inhibition of 55% at a dose of 80 mg/kg p.o. The known steroidal and non-steroidal antiphlogistics, including naproxen, are ineffective in this experimental set-up.

(b) In-vitro inhibition of lipid peroxidation

Further convincing evidence of the pronounced protective action of the compounds according to the invention against aggressive oxygen radicals is provided by the thiobarbituric acid test of A. Ottolenghi (Arch. Biochem. Biophys. 79 (1959) pp. 355-363). Using this in-vitro method, the influence on microsomal and mitochondrial lipid peroxidation by antioxidatively active preparations can be determined from the malonodialdehyde produced on oxidative degradation of membrane-bound, polyunsaturated fatty acids.

Here too, the compounds of the formula I exerted a strong inhibitory action. For example, $IC_{50}$ values of $5 \times 10^{-7}$ and $4 \times 10^{-6}$ mol/l were determined for the compound of Example 1 using rat liver microsomes and mitochondria respectively.

6. Inhibition of 5-lipoxygenase

The inhibitory action of the compounds according to the invention on 5-lipoxygenase-catalyzed degradation of arachidonic acid was determined, as usual, in in-vitro experiments on isolated polymorphonuclear human granulocytes. To this purpose, cells stimulated by calcium ionophor A 23 187 (Calbiochem GmbH, Frankfurt/Main, FRG, Biochemical and Immunochemical Catalog 1985, p. 284) were incubated with $^{14}C$-labeled arachidonic acid, and the major radioactive degradation products of arachidonic acid formed after 15 minutes at 37° C. by biotransformation, 5-hydroxyeicosatetraenoic acid (5-HETE) and leucotriene $B_4$ ($LTB_4$), which has a particularly strong pro-inflammatory action, were determined quantitatively with the aid of a radio monitor after separation by high-pressure liquid chromatography (HPLC). In this experimental set-up, it was possible to significantly inhibit the formation of both $LTB_4$ and 5-HETE, and accordingly the degradation of arachidonic acid by 5-lipoxygenase, by pre-incubating the granulocytes for 15 minutes with, for example, the compound of Example 1 in the concentration range between $10^{-5}$ and $10^{-6}$ mol/l.

We claim:

1. An imidazo- or triazolothiadiazine of the formula I

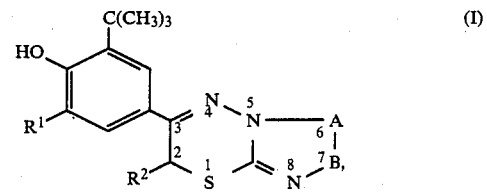

in which $R^1$ is a straight-chain or branched alkyl group having 1 to 4 carbon atoms, $R^2$ is a hydrogen atom or an alkyl radical having 1 to 3 carbon atoms, and —A—B is a two-membered structural element in the five-membered ring and represents —CH$_2$—CH$_2$—, —CH=CH—, —CH=N—, —CH$_2$—CO— or CO—CH$_2$—, or a physiologically acceptable acid-addition salt thereof.

2. A compound as claimed in claim 1, wherein the structural element —A—B is an ethylene or vinylene group, or either A or B is a carbonyl group and the other member is a methylene group.

3. A compound as claimed in claim 1, wherein $R^1$ is a tert-butyl radical and $R^2$ is hydrogen or methyl.

4. A compound as claimed in claim 1, wherein $R^1$ is a tert-butyl radical and $R^2$ is hydrogen, 3-(3,5-di-tert,butyl-4-hydroxyphenyl)-6,7-dihydro-2H-imidazo-[2,1b][1,3,4]thiadiazine.

5. A pharmaceutical composition for the treatment or prevention of an inflammatory disorder in a warm blooded animal comprising an effective amount for said treatment or prevention of a compound of formula I of claim 1, or a physiologically acceptable acid-addition salt thereof, with a physiologically acceptable carrier.

6. A method of treating or preventing inflammatory disorders in a warm-blooded animal, which comprises administering thereto an effective amount of a compound of formula I of claim 1 or a physiologically acceptable acid-addition salt thereof with or without a pharmaceutically acceptable carrier.

7. A method of treating or preventing inflammatory rheumatic disorders in a warm-blooded animal, which comprises administering thereto an effective amount of a compound of formula I of claim 1 or a physiologically acceptable acid-addition salt thereof without or without a pharmaceutically acceptable carrier.

8. A method of using a compound of formula I of claim 1 or a physiologically acceptable acid-addition salt thereof as an anti-inflammatory drug with immunomodulating properties, which comprises administering an effective amount of the compound of claim 1 or the salt thereof to a host, with or without a pharmaceutically acceptable carrier.

9. A method of using a compound of formula I of claim 1 or a physiologically acceptable acid-addition salt thereof as an anti-inflammatory drug with oxygen radical-deactivating properties, which comprises administering an effective amount of the compound of claim 1 or the salt thereof to a host, with or without a pharmaceutically acceptable carrier.

10. A method of using a compound of formula I of claim 1 or a physiologically acceptable acid addition salt thereof as an anti-inflammatory drug that inhibits arachidonic acid degradation induced by 5-lipoxygenase in a warm-blooded animal, which comprises administering an effective amount of said compound to said warm-blooded animal, with or without a pharmaceutically acceptable carrier.

* * * * *

UNITED STATES PATENT AND TRADEMARK OFFICE
CERTIFICATE OF CORRECTION

PATENT NO. : 4,891,374

DATED : January 2, 1990

INVENTOR(S) : WERNER THORWART et al.

It is certified that error appears in the above-identified patent and that said Letters Patent is hereby corrected as shown below:

Claim 4, column 4, line 62, replace "tert,butyl" with --tert.butyl--.

Claim 7, column 15, line 13, replace "without," first occurrence, with --with--.

Signed and Sealed this

Twenty-third Day of July, 1991

Attest:

HARRY F. MANBECK, JR.

*Attesting Officer*

*Commissioner of Patents and Trademarks*